US00PP19445P2

(12) United States Plant Patent
Hurkman

(10) Patent No.: US PP19,445 P2
(45) Date of Patent: Nov. 11, 2008

(54) ***IMPATIENS* PLANT NAMED 'BALFIEBUR'**

(50) Latin Name: *Impatiens walleriana*
Varietal Denomination: Balfiebur

(75) Inventor: Margaret M. Hurkman, Santa Maria, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/895,172

(22) Filed: Aug. 23, 2007

(51) Int. Cl.
*A01H 5/00* (2006.01)

(52) U.S. Cl. ..... Plt./317

(58) Field of Classification Search ..... Plt./317
See application file for complete search history.

(56) References Cited

PUBLICATIONS

Canada Plant Breeders'Rights application No. 07–5867 filed Apr. 12, 2007. Copy of published information from Canada Plant Breeders'Rights Office web site attached.

*Primary Examiner*—Kent L. Bell
*Assistant Examiner*—June Hwu
(74) *Attorney, Agent, or Firm*—Audrey Charles

(57) ABSTRACT

A new and distinct cultivar of *Impatiens* plant named 'Balfiebur', characterized by its double type dark burgundy-colored flowers, dark green-colored foliage, and vigorous, upright-mounded growth habit.

1 Drawing Sheet

Latin name of genus and species of plant claimed: *Impatiens walleriana.*
Variety denomination: 'Balfiebur'.

BACKGROUND OF THE INVENTION

The present invention relates to a new and distinct cultivar of *Impatiens* plant botanically known as *Impatiens walleriana* and hereinafter referred to by the cultivar name 'Balfiebur'.

The new cultivar originated in a controlled breeding program in Arroyo Grande, Calif. during November 2004. The objective of the breeding program was the development of *Impatiens* cultivars with fully double-type flowers, attractive flower and foliage coloration, and a freely branching, compact growth habit.

The new *Impatiens* cultivar is the result of cross-pollination. The female (seed) parent of the new cultivar is the proprietary *Impatiens walleriana* breeding selection designated 5018-6, not patented, characterized by its semi-double type dark burgundy-colored flowers, dark green-colored foliage, and upright-mounded growth habit. The male (pollen) parent of the new cultivar is the proprietary *Impatiens walleriana* breeding selection designated 3466-1-1-1-1, not patented, characterized by its double type dark burgundy-colored flowers, dark green-colored foliage, and upright-mounded growth habit. The new cultivar was discovered and selected as a single flowering plant within the progeny of the above stated cross-pollination during August 2005 in a controlled environment at Arroyo Grande, Calif.

Asexual reproduction of the new cultivar by terminal stem cuttings since August 2005 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balfiebur' as a new and distinct cultivar of *Impatiens* plant:

1. Double type, dark burgundy-colored flowers;
2. Dark green-colored foliage; and
3. Vigorous, upright-mounded growth habit.

Plants of the new cultivar differ from plants of the female parent primarily in flower form and leaf size and from plants of the male parent primarily in flower size. Plants of the new cultivar have smaller leaves than the female parent and larger flowers than the male parent.

Of the many commercially available *Impatiens* cultivars known to the inventor, the most similar in comparison to the new cultivar is SILHOUETTE Purple 'Silte Pur', not patented. However, in side by side comparisons, plants of the new cultivar differ from plants of 'Silte Pur' in the following characteristics:

1. Plants of the new cultivar are taller than plants of 'Silte Pur'; and
2. Plants of the new cultivar have larger leaves, as measured by leaf length, than plants of 'Silte Pur'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balfiebur'. The plants were grown in 4.5 inch pots for 7 weeks in a greenhouse at West Chicago, Ill. Plants were given one pinch at transplant.

DETAILED BOTANICAL DESCRIPTION

Figure 1:
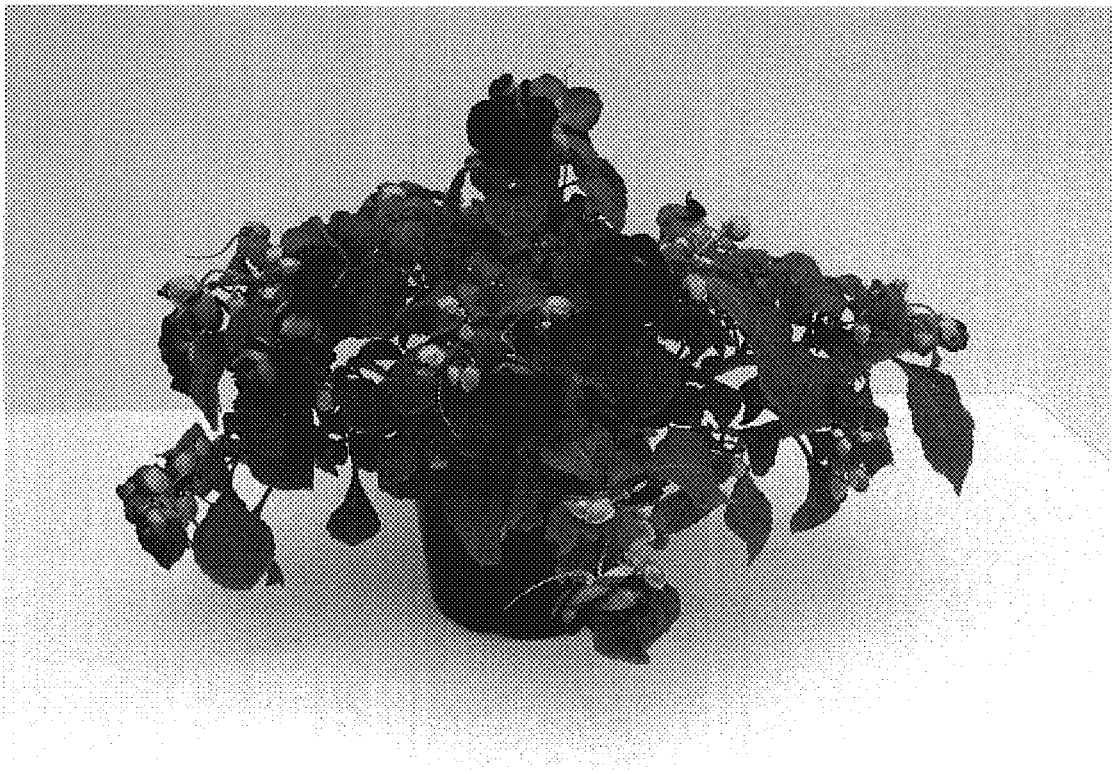
FIG. 1 illustrates a side view of the overall growth and flowering habit of 'Balfiebur'.
Figure 2:
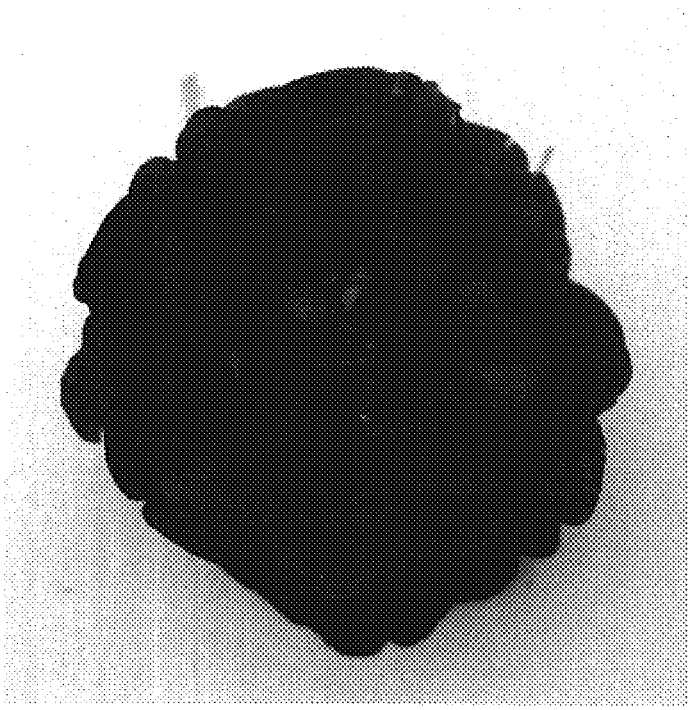
FIG. 2 illustrates a close-up view of an individual flower of 'Balfiebur'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein in The R.H.S. Colour Chart of The Royal Horticultural Society, London, England, 2001 edition, except where general color terms of ordinary significance are used. The color values were determined on May 4, 2007 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 7 weeks utilizing a soilless growth medium. Plants were given on pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Impatiens walleriana* cultivar Balfiebur.

Parentage:

*Female parent.*—Proprietary *Impatiens walleriana* breeding selection designated 5018-6, not patented.

*Male parent.*—Proprietary *Impatiens walleriana* breeding selection designated 3466-1-1-1-1, not patented.

Propagation:

*Type cutting.*—Terminal stem.

*Time to initiate roots.*—Approximately 7 to 8 days.

*Time to produce a rooted cuttings.*—Approximately 21 to 24 days.

*Root description.*—Fibrous.

*Rooting habit.*—Freely branching.

Plant description:

*Commercial crop time.*—Approximately 5 to 7 weeks from a rooted cutting to finish in a 10 cm pot.

*Growth habit and general appearance.*—Vigorous, upright-mounded.

*Size.*—Height from soil level to top of plant plane: Approximately 13.4 cm. Width: Approximately 32.3 cm.

*Branching habit.*—Freely branching, pinching improves basal branching. Quantity of main branches per plant: Approximately 5.

*Branch.*—Strength: Moderately strong. Length: Approximately 14.9 cm. Diameter at central internode: Approximately 5.0 mm. Length of central internode: Approximately 1.7 cm. Texture: Glabrous. Color of young and mature stems: 145D with streaks of 187C.

Foliage description:

*General description.*—Quantity of leaves per main branch: Approximately 9. Fragrance: None. Form: Simple. Arrangement: Alternate.

*Leaves.*—Aspect: Acute angle to stem, becomes perpendicular with age. Shape: Ovate. Margin: Crenate, ciliate. Apex: Acute. Base: Attenuate. Venation pattern: Pinnate. Length of mature leaf at center of stem: Approximately 5.0 cm. Width of mature of leaf at center of stem: Approximately 3.8 cm. Texture of upper surface: Sparsely pubescent. Texture of lower surface: Glabrous. Color of upper surface of young and mature foliage: 137B with venation of 137C. Color of lower surface of young and mature foliage: 191C with splotches of N187B and venation of 145D.

*Petiole.*—Length: Approximately 2.1 cm. Diameter: Approximately 2.0 mm. Texture: Glabrous. Color: 145D with streaks of 187C.

Flowering description:

*Flowering habit.*—'Balfiebur' is freely flowering under outdoor growing conditions with substantially continuous blooming from spring through autumn and year-round in greenhouse environment.

*Lastingness of individual flower on the plant.*—Approximately 6 to 7 days.

Flower description:

*General description.*—Type: Double. Quantity per plant: Approximately 14. Fragrance: None.

*Bud.*—Rate of opening: Generally takes 2 to 3 days for bud to progress from first color to fully open flower. Quantity showing color per plant: Approximately 8.

*Bud just before opening.*—Shape: Ovoid. Length: Approximately 1.5 cm. Diameter: Approximately 1.2 cm. Color: 71D.

*Corolla.*—Shape: Hemispherical. Width: Approximately 4.1 cm. Depth. Approximately 2.1 cm. Borne: Above and below foliage.

*Petals.*—Quantity: 29. Shape: Obovate, innermost irregular. Aspect: Flat. Appearance: Iridescent. Margin: Entire. Apex: Obtuse, some are emarginate. Base: Attenuate. Length of outermost petal: Approximately 2.1 cm. Width of outermost petal: Approximately 2.2 cm. Length of innermost petals: Approximately 9.1 mm. Width of innermost petals: Approximately 3.5 mm. Texture of upper and lower surfaces: Glabrous. Color of upper surface when first and fully open: 71A. Color of lower surface when first and fully open: 71B.

*Spur.*—Quantity: 1 per flower. Length: Approximately 3.5 cm. Diameter at tip: Less than 1 mm. Diameter at base: Approximately 2.0 mm. Texture: Glabrous. Color: 145B with an overlay of 185B and tip of 185A.

*Peduncle.*—Strength: Moderately strong. Aspect: Acute angle to stem. Length: Approximately 3.4 cm. Diameter: Approximately 2.0 mm. Texture: glabrous. Color: 145B with a faint overlay of 185B.

*Sepals.*—Quantity per flower: 4 with one fused to base of upper petal. Shape of lateral sepals: Lanceolate. Shape of lower sepal: Ovate. Apex of all sepals: Acute. Length of lateral sepals: Approximately 3.0 mm. Width of lateral sepals: Approximately 1.0 mm. Length of lower sepal: Approximately 1.5 cm. Width of lower sepal: Approximately 1.2 cm. Texture of upper and lower surfaces of all sepals: Glabrous. Color of lateral sepals: 144A. Color of lower sepal: 69B with tip of 144A.

*Reproductive organs.*—None observed.

Seed and fruit production: Neither seed not fruit production has been observed.

Disease and pest resistance: Resistance to pathogens and pests common to *Impatiens* has not been observed.

What is claimed is:

1. A new and distinct cultivar of *Impatiens* plant named 'Balfiebur', substantially as herein shown and described.

* * * * *